United States Patent [19]

Guay et al.

[11] 4,400,978

[45] Aug. 30, 1983

[54] ELECTRONIC HYDROMETER AND METHOD OF DETERMINING THE DENSITY OF A LIQUID

[75] Inventors: Raymond Guay, Dollard des Ormeaux; Pierre R. Moffatt, Ste-Thérèse, both of Canada

[73] Assignee: Louis Boivin, Quebec, Canada

[21] Appl. No.: 298,507

[22] Filed: Sep. 1, 1981

[51] Int. Cl.³ ............................................. G01N 9/20
[52] U.S. Cl. ...................................................... 73/453
[58] Field of Search ....................... 73/32 R, 451, 453

[56] References Cited

U.S. PATENT DOCUMENTS

| | | | |
|---|---|---|---|
| 3,407,666 | 10/1968 | Glassey | 73/453 |
| 3,766,786 | 10/1973 | Gehatia | 73/453 |
| 3,964,317 | 6/1976 | Blanchard | 73/453 |

*Primary Examiner*—James J. Gill
*Attorney, Agent, or Firm*—Oblon, Fisher, Spivak, McClelland & Maier

[57] ABSTRACT

An electronic hydrometer for determining the density of a liquid, the hydrometer comprising a housing having a liquid receiving chamber and means to insert a liquid of which the density is to be determined in the chamber. A float having a known weight is disposed in the chamber. A connecting shaft is secured to the float and retained for guided displacement along its longitudinal axis in response to introduction of a predetermined quantity of liquid in the chamber. A sensor is associated with a shaft for detecting a reference position of the shaft. A permanent magnet is mounted in proximity of the shaft and has a magnetic core and a displaceable coil about the core. The coil is secured to the shaft. An electronic circuit means automatically adjusts the value of a current flowing in the coil to displace the coil and the shaft relative to the reference position. The value of the adjusted current is calibrated by the circuit to generate an output signal indicative of the density of the liquid in the chamber.

11 Claims, 3 Drawing Figures

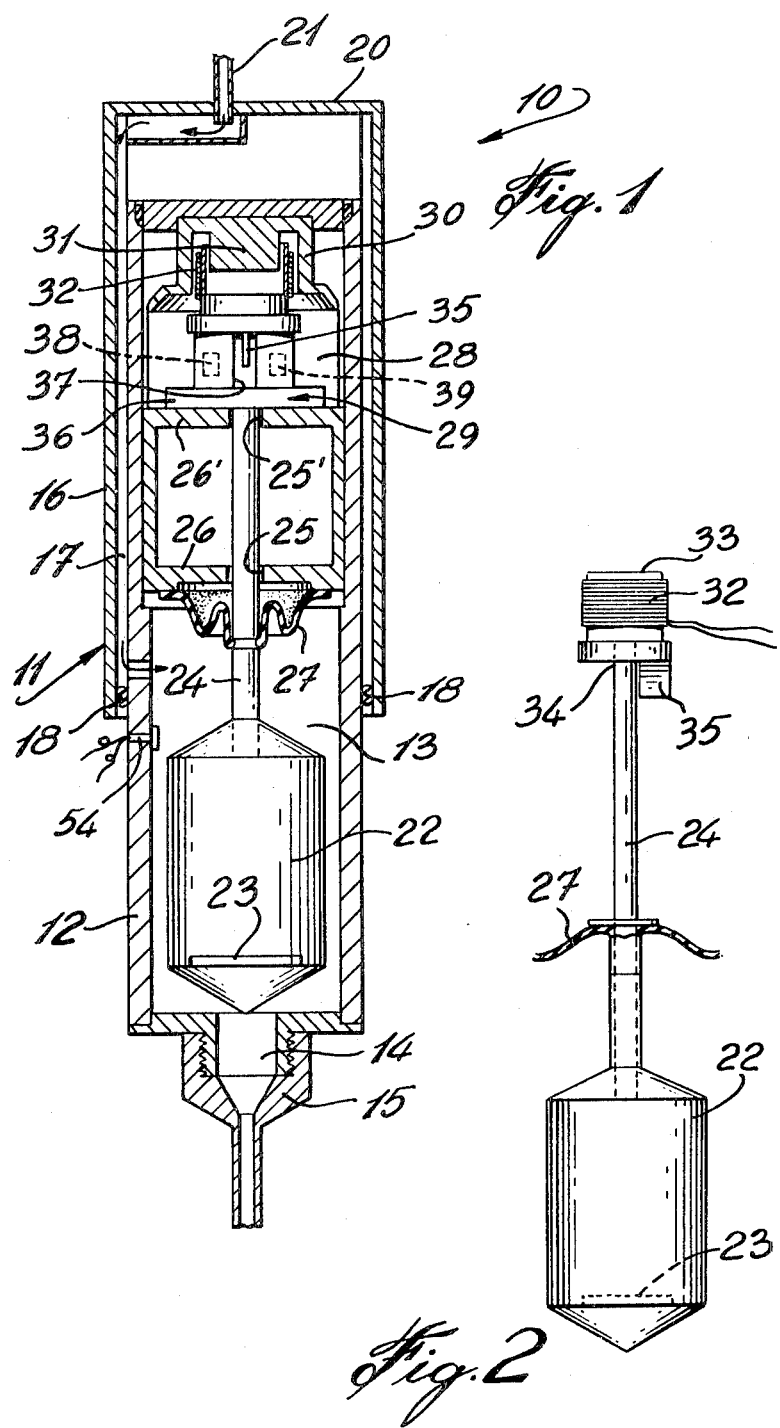

ELECTRONIC HYDROMETER AND METHOD OF DETERMINING THE DENSITY OF A LIQUID

BACKGROUND OF THE INVENTION

1. Field of Invention

The present invention relates to hydrometers and more particularly to an electronic hydrometer having an electronic circuit capable of automatically controlling the position of a float by means of a variable current supply and providing an output signal indicative of the density of a liquid.

2. Description of Prior Art

Various hydrometer constructions are known. The present invention utilizes an electronic hydrometer with a permanent magnet wherein the current flowing through the force coil is utilized to displace the float to restore to a neutral position. U.S. Pat. No. 3,964,317 does utilize a permanent magnet in combination with the float. However, the device operates in a different manner than the present invention wherein the current generated by the circuit associated with the coil generates heating losses corresponding to the difference between the density of the liquid and the density corresponding to a neutral buoyancy position of the float. The construction of the hydrometer and electronic circuit of this patent is quite different from that of the present invention although there are similarities in the use of a permanent magnet, but the sensor and the electronic circuit operate entirely differently from that of the present invention.

SUMMARY OF THE INVENTION

It is a feature of the present invention to provide an electronic hydrometer which is capable of accurately measuring the density of a liquid quickly and automatically and providing an output calibrated signal indicative of such density.

According to the above feature, from a broad aspect, the present invention provides an electronic hydrometer comprising a housing having a liquid receiving chamber and means to insert a liquid of which the density is to be determined in the chamber. A float having a known weight is disposed in the chamber. A connecting shaft is secured to the float and retained for guided displacement along its longitudinal axis in response to introduction of a predetermined quantity of liquid in the chamber. A sensor is associated with a shaft for detecting a reference position of the shaft. A permanent magnet is mounted in proximity of the shaft and has a magnetic core and a displaceable coil about the core. The coil is secured to the shaft. An electronic circuit means automatically adjusts the value of a current flowing in the coil to displace the coil and the shaft relative to the reference position. The value of the adjusted current is calibrated by the circuit to generate an output signal indicative of the density of the liquid in the chamber.

BRIEF DESCRIPTION OF THE DRAWINGS

A preferred embodiment of the present invention will now be described with reference to the accompanying drawings in which:

FIG. 1 is a section view of the electronic hydrometer of the present invention;

FIG. 2 is a side view of the float showing the shaft connected thereto with the coil and part of the sensor connected to the end of the shaft.

DESCRIPTION OF PREFERRED EMBODIMENTS

Figure 3:
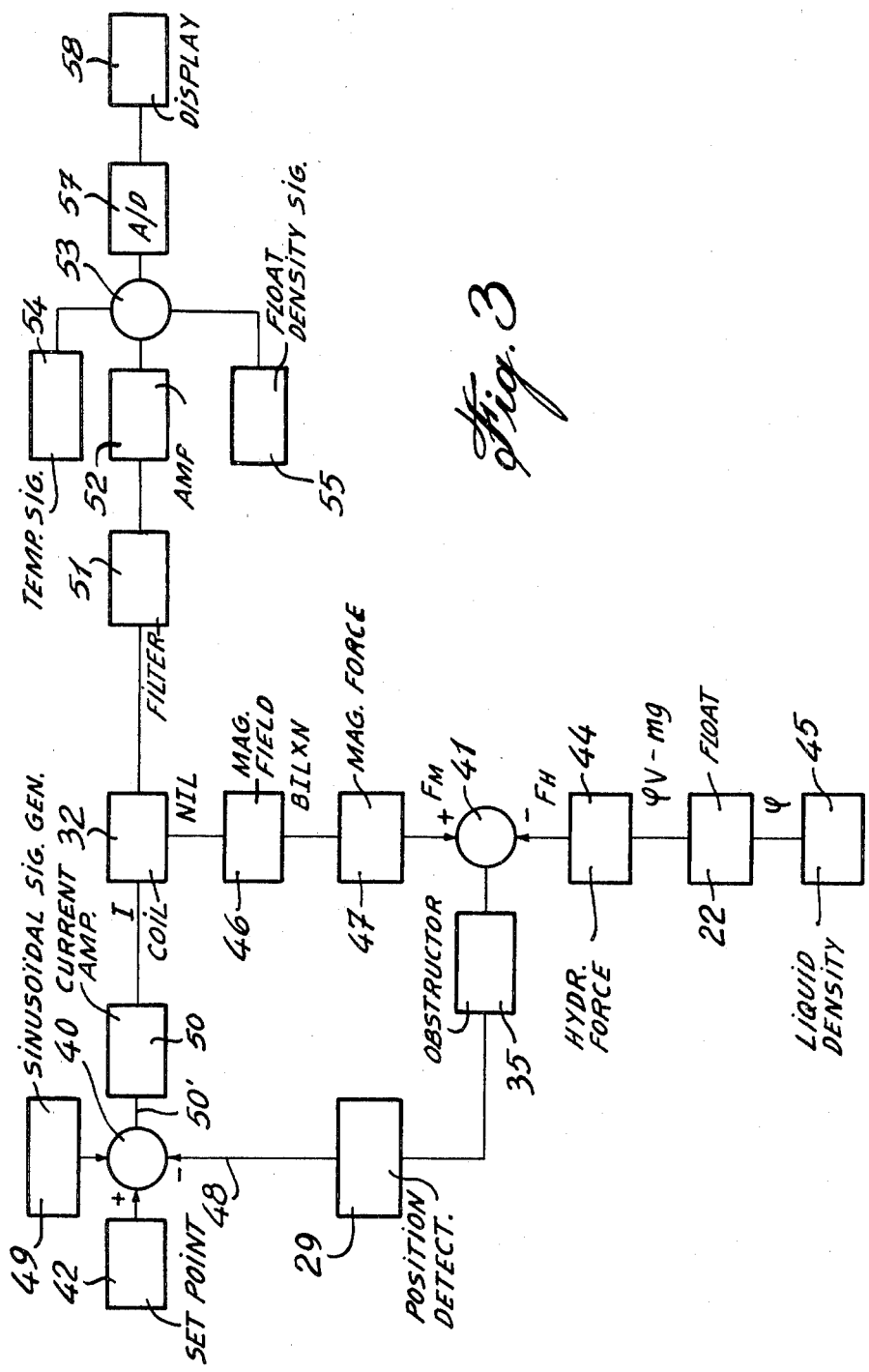
FIG. 3 is a schematic flow diagram showing the operation of the electronic hydrometer.

Referring now to the drawings, and more particularly to FIGS. 1 and 2, there is shown generally at 10 the electronic hydrometer of the present invention. The hydrometer comprises a housing 11 which is formed by an elongated cylindrical tube 12 defining in a lower portion thereof a liquid receiving chamber 13 having an inlet 14 at a lower end thereof to admit a liquid within the chamber 13 through a spout tube 15. An outer cylindrical sleeve 16 is secured about a portion of the tube 12 in spaced relationship therewith whereby to define a sealed space 17 between an inner face thereof and the outer face of the cylindrical tube 12. A seal 18 is secured about the lower end of the outer cylindrical sleeve 16 between the inner face of the sleeve and the outer face of the tube to constitute the sealed space 17.

A plurality of apertures 19 are provided about the cylindrical tube in registry with the sealed space 17 whereby to communicate the inner area of the liquid receiving chamber 13 with the sealed space 17. The outer cylindrical sleeve 16 has a top wall 20 provided with a nipple 21 to which a suction device (not shown) is connected whereby to syphon liquid into the liquid receiving chamber 13 by evacuating air therefrom whereby liquid is drawn up the spout tube into the liquid receiving chamber 13, as the air is evacuated from the chamber 13 through the apertures 19 and the sealed space 17 and into the suction device.

A float 22 is disposed in the liquid receiving chamber 13 and is provided with a calibrated weight 23 whereby the float has a known density. A connecting shaft 24 is secured to an upper end of the float 22 and extends longitudinally in the cylindrical tube 12. The shaft is guided through apertures 25 and 25' provided in two spaced apart transverse guide walls 26 and 26' respectively. The shaft is closely spaced in these apertures whereby it is maintained substantially stable along its longitudinal axis.

A diaphragm seal 27 is secured about the shaft below the transverse wall 26 whereby to prevent any liquid in the liquid receiving chamber 13 from seeping into a component receiving chamber 28 located thereabove.

A sensor device 29 is secured in the component receiving chamber 28 and is associated with the shaft 24 to detect a reference position of the shaft. A permanent magnet 30 is mounted above the shaft 24 in the component receiving chamber 28. The permanent magnet 30 has a magnetic center core 31 about which a coil 32 is displaceably positioned. The coil 32 is mounted on a coil supporting cylinder 33 which is secured to the top end 34 of the shaft 24. Also mounted to the top end 34 of the shaft 24 is a light beam obstruction plate 35 which forms part of the sensor device 29.

The sensor device 29 comprises a sensor member 36 defining a slot 37 therein through which the obstructing plate 35 is displaced. A light source 38 is positioned to one side of the slot 37 to direct a light beam thereacross to a photocell 39 secured on the other side of the slot. Therefore, as the obstruction plate 35 moves into the slot and obstructs the light beam, the photocell will detect the amount of obstruction as it will receive more or less light or none at all, if completely obstructed and generate a signal proportional to the amount of light received, thus permitting detection of the position of the shaft and making the correction.

Referring now to FIG. 3, there is shown the electronic circuit incorporated with the hydrometer and its purpose is to automatically adjust the value of the current flowing into the coil 32 whereby to displace the coil and thereby adjust the position of the shaft 24. This is done by sensing the position of the obstruction plate 35 with respect to a predetermined position thereof in the slot 37. The current flowing through the coil 32 is automatically adjusted until the obstruction plate 35 is at a predetermined position which is sensed by the output signal generated by the photocell 39. The value of the adjusted current (the current required to position the plate 35 at its predetermined position) is then calibrated by the electronic circuit to generate an output signal indicative of the density of the liquid in the chamber.

As shown in FIG. 3 the coil 32 is connected in a loop current generating circuit 43 provided with a first summator 40 and a second summator 41. A reference signal is provided to the first summator 40 by the reference circuit 42 and it provides a signal representative of the desired reference or predetermined position of the obstructing plate 35. The current generating circuit 43 automatically adjusts the value of the current flowing through the coil 32 until the hydraulic force $F_H$ on the shaft 24, due to the liquid introduced in the chamber 13, equals the magnetic force $F_M$ of the permanent magnet 30. The value of these forces are illustrated in block form wherein the hydraulic force $F_H$ is indicated by block 44 and is applied to summator 41. $F_M$ is the resultant of the liquid force indicated by block 45 acting on the float 22. The magnetic force is indicated schematically by the magnetic field, indicated schematically by block 46, in the magnet providing the resulting magnetic force indicated by block 47. The flow diagram also illustrates the obstructing plate 35 connected to the output of the summator 41 and cooperating with the sensor 29 feeding an output error signal on its output 48 to the first summator. A sinusoidal signal generator 49 is also connected to the first summator 40 to impart an oscillatory movement to the shaft 24 whereby there is no frictional engagement between the shaft and the apertures 25 and 25' in the guide walls 26 and 26'. This oscillatory movement prevents the shaft from sticking to the wall.

The output 50' of the first summator 40 is fed to a current amplifier 50 which increases the current applied thereto from the first summator. The current is stabilized when the signal on line 48 equals the reference signal of the reference circuit 42.

The current flowing through the coil 32 is also fed to a filter circuit 51 where the sinusoidal signal is filtered out. The output of the filter is then fed to an amplifier 52 and to a third summator 53. A thermistor 54 is connected to the liquid receiving chamber 13 to sense the temperature of the circuit and provides a signal indicative thereof to the third summator 55 whereby the resultant current signal can be calibrated. Also, a weight compensating circuit 55 provides a reference signal to the third summator 53 to compensate for the weight or the known density of the float. The signal at the output 56 of the summator 53 is a calibrated output signal and it is fed to an analog digital converter circuit 57 whereby the signal is converted to a suitable form for activating an LED display 58 or other suitable display devices to visually indicate the density of the liquid measured.

All of the electronics components forming part of the flow diagram of FIG. 3 may be conveniently housed in the component receiving chamber 28 or outside the hydrometer. It is also within the ambit of the present invention to provide any obvious modifications of the embodiment described herein. For example, the air may be syphoned from the liquid receiving chamber 13 by other means than that herein described and the sensor device and permanent magnet may be positioned differently with respect to the shaft, provided their use is fulfilled.

Mathematically expressed, the operation of the current generating circuit is to adjust the value of the current flowing through the coil unit $F_H = F_M$ where $F_H$ is the hydraulic force on the shaft due to the liquid, and $F_M$ is the magnetic force of the permanent magnet and wherein $F_H \alpha \rho$ where $\rho$ is the density of the liquid, and further wherein $F_M \alpha I$ where I is the value of the current flowing in the coil.

We claim:

1. An electronic hydrometer comprising a housing having a liquid receiving chamber, means to insert a liquid of which the density is to be determined in said chamber, a float having a known weight being disposed in said chamber, a connecting shaft secured to said float and maintained axially aligned in said housing by spaced apart guide slots for guided displacement along its longitudinal axis in response to introduction of a predetermined quantity of liquid in said chamber, a sensor associated with said shaft for detecting a reference position of said shaft, a permanent magnet mounted in proximity of said shaft and having a magnetic core and a displaceable coil about said core, said coil being secured to said shaft, an electronic circuit means to automatically adjust the value of a current flowing in said coil to displace said coil and said shaft relative to said reference position, the value of said adjusted current being calibrated by said circuit to generate an output signal indicative of the density of said liquid in said chamber and a sinusoidal signal connected to said coil to impart to said shaft small oscillations whereby to prevent frictional retention of said shaft through said guide slots.

2. A hydrometer as claimed in claim 1 wherein said sensor is an optical sensor comprising a light source to generate a light beam and a photocell to detect the presence of said beam, and a beam obstruction plate secured to said shaft and aligned for displacement across said beam in response to displacement of said shaft.

3. A hydrometer as claimed in claim 2 wherein said housing is further provided with a component receiving chamber for housing said permanent magnet and sensor, said shaft extending from said liquid receiving chamber to said component receiving chamber, and a seal about said shaft to isolate said liquid receiving chamber from said component receiving chamber.

4. A hydrometer as claimed in claim 1 wherein a thermistor is secured in said liquid receiving chamber to sense the temperature of a liquid positioned therein and provide a signal indicative thereof to said electronic circuit means for calibrating said value of said adjusted current.

5. A hydrometer as claimed in claim 1 wherein said means to insert a liquid in said chamber comprises a suction device having a conduit connected to said liquid receiving chamber, said liquid receiving chamber having a spout end for admitting liquid therein, and a seal about said shaft to prevent air ingress in said chamber when liquid is drawn therein.

6. A hydrometer as claimed in claim 5 wherein said housing is an elongated cylindrical tube, said liquid receiving chamber being disposed in a lower portion thereof, an outer cylindrical sleeve secured about a portion of said tube and in spaced relation therewith, seal means to provide a sealed space between said tube and said sleeve, apertures in said tube in a top portion of said liquid receiving chamber and in registry with said sealed space, said suction device being connected to said sealed space to aspirate air out of said liquid receiving chamber through said apertures.

7. A hydrometer as claimed in claim 1 wherein said electronic circuit means comprises a current generating circuit for automatically adjusting the value of the current flowing through said coil until, $$F_H = F_M$$

where $F_H$ is the hydraulic force on the shaft due to the liquid, and $F_M$ is the magnetic force of the permanent magnet and wherein $$F_H \alpha \rho$$

where $\rho$ is the density of the liquid, and further wherein $$F_M \alpha I$$

where I is the value of the current flowing in the coil.

8. A hydrometer as claimed in claim 7 wherein said current generating circuit comprises a first summator, an input signal generated by said sensor fed to said first summator indicative of the location of the reference position of said shaft, said summator generating an error signal to an amplifier to modify the value of said current flowing through said coil, and a second summator receiving a first signal indicative of the magnetic force of said permanent magnet and a second signal of the hydraulic force acting on said shaft and providing said error signal to said first summator until said circuit is in balance where $F_H = F_M$.

9. A hydrometer as claimed in claim 8 wherein said circuit means further comprises a calibration and output circuit to calibrate and generate said output signal, said calibration and output circuit being fed by said current flowing through said coil through said filter circuit to remove the effects of a sinusoidal signal applied to said coil through said first summator, said filtered signal is then amplified through an amplifier and fed to a third summator, a temperature reference signal and a reference signal representative of the weight of said float also connected to said third summator to provide a calibrated output signal indicative of the density of said liquid in said chamber.

10. A hydrometer as claimed in claim 9 wherein said calibrated output signal is connected to an analog/digital converter to provide a digital output signal to a display device to produce a visual display value of said density of said liquid.

11. A method of determining the density of a liquid comprising the steps of
  (i) detecting the displacement of a float in said liquid relative to a reference position associated with said float,
  (ii) displacing the position of said float by controlling the value of a current flowing through a coil connected to said float, said coil being part of a permanent magnet,
  (iii) sensing the position of said float and automatically adjusting the value of said current until the magnetic force $F_M$ of said permanent magnet equals the hydraulic force $F_H$ of said liquid acting on said float,
  (iv) calibrating the value of said current when $F_M = F_H$ to provide an output signal indicative of the density of said liquid,
  (v) guiding said connecting shaft through spaced apart guide slots, and
  (vi) imparting small oscillations to said shaft by applying a sinusoidal signal to said coil thereby to prevent frictional retention of said shaft through said guide slots.

* * * * *